United States Patent
Li

(10) Patent No.: US 10,772,526 B2
(45) Date of Patent: Sep. 15, 2020

(54) APPARATUS AND METHOD FOR DETERMINING WHETHER THE BRAIN IS FATIGUED

(71) Applicant: BOE TECHNOLOGY GROUP CO., LTD., Beijing (CN)

(72) Inventor: Hui Li, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 1012 days.

(21) Appl. No.: 15/029,166

(22) PCT Filed: Oct. 10, 2015

(86) PCT No.: PCT/CN2015/091644
§ 371 (c)(1),
(2) Date: Apr. 13, 2016

(87) PCT Pub. No.: WO2016/188011
PCT Pub. Date: Dec. 1, 2016

(65) Prior Publication Data
US 2017/0112406 A1    Apr. 27, 2017

(30) Foreign Application Priority Data

May 22, 2015  (CN) .......................... 2015 1 0266869

(51) Int. Cl.
*A61B 5/0476*    (2006.01)
*A61B 5/00*    (2006.01)
(Continued)

(52) U.S. Cl.
CPC ........ *A61B 5/0476* (2013.01); *A61B 5/04017* (2013.01); *A61B 5/04018* (2013.01);
(Continued)

(58) Field of Classification Search
CPC ............................. A61B 5/048; A61B 5/0476
See application file for complete search history.

(56) References Cited

U.S. PATENT DOCUMENTS 6,496,724 B1   12/2002  Levendowski et al.
7,299,088 B1 * 11/2007  Thakor .................. A61B 5/048
                                                              600/544
(Continued)

FOREIGN PATENT DOCUMENTS

CN          1771883 A        5/2006
CN        102715889 A       10/2012
(Continued)

OTHER PUBLICATIONS

Discriminating Threshold of Driving Fatigue Based on the Electroencephalography Sample Entropy by Receiver Operating Characteristic Curve Analysis, Journal of Southwest Jiaotong University, vol. 8, No. 1, Feb. 2013 (6 pages).
(Continued)

*Primary Examiner* — Etsub D Berhanu
*Assistant Examiner* — Michael A Catina
(74) *Attorney, Agent, or Firm* — Dave Law Group LLC; Raj S. Dave

(57) ABSTRACT

An apparatus for determining whether the brain is fatigued may include: an electroencephalogram signal collection module for collecting electroencephalogram signals of a testee; a quantization processing module for quantifying the electroencephalogram signals utilizing a sample entropy algorithm to obtain a final sample entropy value of the electroencephalogram signals; and a fatigue state determination module for determining whether the brain of the testee is fatigued according to the final sample entropy value, wherein it is determined that the brain of the testee is
(Continued)

in a fatigue state when the final sample entropy value is within a predetermined range.

9 Claims, 2 Drawing Sheets

(51) Int. Cl.
*A61B 5/04* (2006.01)
*A61B 5/16* (2006.01)

(52) U.S. Cl.
CPC ............... *A61B 5/16* (2013.01); *A61B 5/165* (2013.01); *A61B 5/6803* (2013.01); *A61B 5/6814* (2013.01); *A61B 5/7203* (2013.01); *A61B 5/7405* (2013.01); *A61B 5/7455* (2013.01); *A61B 2503/20* (2013.01)

(56) References Cited

U.S. PATENT DOCUMENTS

| | | | |
|---|---|---|---|
| 2007/0066906 | A1 | 3/2007 | Goldberger et al. |
| 2011/0282230 | A9 | 11/2011 | Liley |
| 2015/0018704 | A1 | 1/2015 | Fang et al. |
| 2015/0032021 | A1 | 1/2015 | Chen et al. |
| 2016/0220783 | A1* | 8/2016 | Garcia Molina ...... A61B 5/048 |

FOREIGN PATENT DOCUMENTS

| | | |
|---|---|---|
| CN | 103610447 A | 3/2014 |
| CN | 103815900 A | 5/2014 |
| CN | 103989485 A | 8/2014 |
| CN | 104146722 A | 11/2014 |
| CN | 104305964 A | 1/2015 |
| CN | 104814735 A | 8/2015 |
| CN | 205107675 U | 3/2016 |

OTHER PUBLICATIONS

Masteral Dissertation, Beijing University of Technology, Jun. 2012 (67 pages).
Written Opinion of the International Searching Authority from corresponding PCT Application No. PCT/CN2015/091644, dated Feb. 6, 2016 (5 pages).
Office Action from corresponding Chinese Application No. 201510266869.5, dated Dec. 21, 2016 (9 pages).
Extended European Search Report from European Application No. 15848147.3 dated Dec. 19, 2018 (9 pages).
Chunxiao Chen et al., Assessment Visual Fatigue of Watching 3DTV using EEG Power Spectral Parameters, vol. 35, No. 5, Dec. 1, 2014, pp. 266-272 (7 pages).
Kar S et al., EEG Signal Analysis for the Assessment and Quantification of Driver's Fatigue, vol. 13, No. 5, Sep. 1, 2010, pp. 297-306 (10 pages).
Y. Tran et al., Increase in Regularity and Decrease in Variability Seen in Electroencephalography (EEG) Signals from Alert to Fatigue During a Driving Simulated Task, Aug. 1, 2008, pp. 1096-1099 (4 pages).
Lian-Yi Zhang et al., Study on Physiological Mental Fatigue with Nonlinear Dynamics, Oct. 18, 2008, pp. 670-673 (4 pages).

* cited by examiner

APPARATUS AND METHOD FOR DETERMINING WHETHER THE BRAIN IS FATIGUED

The present application claims priority of Chinese patent application No. 201510266869.5 filed on May 22, 2015, the content of which is referred to entirely as part of the present application.

TECHNICAL FIELD

Embodiments of the present invention relate to an apparatus and method for determining whether the brain is fatigued.

BACKGROUND

With the rapid development of industrialization technologies, brainwork has become a major work form in nowadays society. However, with fierce competition in modern society and a surge in working pressure, the prolonged, high-intensity and monotonous brainwork may cause brain fatigue. At this time, if the brain is still forced to work continually, the efficiency of learning and working will be reduced, harming human health and also easily leading to accidents.

Current methods for determination of brain fatigue are mainly subjective evaluation and objective evaluation. The subjective evaluation method determines the degree of fatigue according to a worker's physical and neurological feeling symptoms, which is conducted mainly through a questionnaire. The scoring criterion of the subjective evaluation method is vulnerable to subjective factors and not easily unified, and cannot objectively evaluate psychophysiological states during fatigue. The objective evaluation method observes human physical and biochemical indexes by means of auxiliary tools such as instruments, devices or the like, and comprehensively evaluates these indexes to estimate the degree of fatigue. However, the relationship between these physical and biochemical indexes and the degree of fatigue is uncertain with great individual differences, and it is difficult to be objective and quantified.

SUMMARY

According to embodiments of the present invention, there is provided a method and apparatus for determining whether the brain is fatigued, and the fatigue state of the brain may be measured objectively by utilizing the method and apparatus.

According to one aspect of the embodiments of the present invention, there is provided a method for determining whether the brain is fatigued, wherein the method comprises:

S1. collecting electroencephalogram signals of a testee;

S2. quantifying the electroencephalogram signals utilizing a sample entropy algorithm to obtain a final sample entropy value of the electroencephalogram signals;

S3. determining whether the brain of the testee is fatigued according to the final sample entropy value, wherein it is determined that the brain of the testee is in a fatigue state when the final sample entropy value is within a predetermined range.

According to an exemplary embodiment of the present invention, the electroencephalogram signals of the testee may be collected in real time.

According to an exemplary embodiment of the present invention, the predetermined range is [0,0.8].

In the step S3, when the final sample entropy value is within the range (0.8,1], it is determined that the brain of the testee is in an active state, and then it proceeds to the step S1.

According to an exemplary embodiment of the present invention, the predetermined range comprises a first predetermined sub-range [0, 0.5] and a second predetermined sub-range (0.5, 0.8]. When the final sample entropy value is within the first predetermined sub-range, it is determined that the brain of the testee is in an excessive fatigue state, and when the final sample entropy value is within the second predetermined sub-range, it is determined that the brain of the testee is in a mild fatigue state.

According to an exemplary embodiment of the present invention, when it is determined in the step S3 that the brain of the testee is in a fatigue state, the method further comprises:

S4. generating reminding information.

According to the exemplary embodiment of the present invention, the reminding information comprises first reminding information and second reminding information, and the step S4 comprises: generating the first reminding information when the final sample entropy value is in the range [0, 0.5], and generating the second reminding information when the final sample entropy value is in the range (0.5, 0.8]. For example, the first reminding information and the second reminding information may be different from each other.

According to an exemplary embodiment of the present invention, the reminding information comprises audio reminding information and/or vibration reminding information.

According to an exemplary embodiment of the present invention, the reminding information comprises the vibration reminding information, which is applied to Fengchi acupoint of the testee in the step S4.

According to an exemplary embodiment of the present invention, the step S2 comprises:

S21. filtering the electroencephalogram signals to remove noise interference;

S22. quantifying the electroencephalogram signals without noises by utilizing a sample entropy algorithm, to obtain an initial sample entropy value;

S23. performing normalization processing on the initial sample entropy value to obtain the final sample entropy value.

According to another aspect of the embodiments of the present invention, there is provided an apparatus for determining whether the brain is fatigued, wherein the apparatus comprises:

an electroencephalogram signal collection module for collecting electroencephalogram signals of a testee;

a quantization processing module for quantifying the electroencephalogram signals utilizing a sample entropy algorithm to obtain a final sample entropy value of the electroencephalogram signals; and a fatigue state determination module for determining whether the brain of the testee is fatigued according to the final sample entropy value, wherein it is determined that the brain of the testee is in a fatigue state when the final sample entropy value is within a predetermined range.

According to an exemplary embodiment of the present invention, an input terminal of the quantization processing module is connected with an output terminal of the electroencephalogram signal collection module.

According to an exemplary embodiment of the present invention, an input terminal of the fatigue state determination module is connected with an output terminal of the quantization processing module.

According to an exemplary embodiment of the present invention, the predetermined range is [0,0.8], and when the final sample entropy value is within the range (0.8,1], the fatigue state determination module determines that the brain of the testee is in an active state.

According to an exemplary embodiment of the present invention, the electroencephalogram signal collection module comprises a main collection electrode for being disposed at a position of the prefrontal cortex of the testee, and a first communication unit for outputting the electroencephalogram signals to the quantization processing module. The main collection electrode is for collecting the electroencephalogram signals of the testee and electrically connected to the first communication unit, the quantization processing module comprises a second communication unit for communicating with the first communication unit and a processing unit for performing quantization of the electroencephalogram signals. The first communication unit is formed as the output terminal of the electroencephalogram signal collection module, and the second communication unit is formed as the input terminal of the quantization processing module.

According to an exemplary embodiment of the present invention, both the first communication unit and the second communication unit are wireless communication units.

According to an exemplary embodiment of the present invention, the electroencephalogram signal collection module further comprises a reference electrode for being disposed behind the ear(s) of the testee and for collecting electroencephalogram signals of the testee, the reference electrode also being electrically connected with the first communication unit.

According to an exemplary embodiment of the present invention, the quantization processing module further comprises a filtering unit and a post-processing unit, the filtering unit being connected with the second communication unit to receive the electroencephalogram signals and the filtering unit being used for filtering the received electroencephalogram signals to remove noise interference, the processing unit being used for quantifying the electroencephalogram signals without noises by utilizing a sample entropy algorithm to obtain an initial sample entropy value, the post-processing unit being used for performing normalization processing on the initial sample entropy value to obtain the final sample entropy value.

According to an exemplary embodiment of the present invention, the predetermined range comprises a first predetermined sub-range [0, 0.5] and a second predetermined sub-range (0.5, 0.8]. When the final sample entropy value is within the first predetermined sub-range, it is determined that the brain of the testee is in an excessive fatigue state, and when the final sample entropy value is within the second predetermined sub-range, it is determined that the brain of the testee is in a mild fatigue state.

According to an exemplary embodiment of the present invention, the apparatus further comprises a reminding information generation module, and the fatigue state determination module can generate a reminding control signal when the brain of the testee is determined to be in a fatigue state, and send the reminding control signal to the reminding information generation module which can generate reminding information according to the reminding control signal.

According to an exemplary embodiment of the present invention, the reminding control signal comprises a first reminding control signal and a second reminding control signal, and the fatigue state determination module can generate the first reminding control signal when the final sample entropy value is within the range [0, 0.5] and generate the second reminding control signal when the final sample entropy value is within the range (0.5, 0.8]. The reminding information comprises first reminding information and second reminding information, and the reminding information generation module can generate the first reminding information upon receipt of the first reminding control signal and generate the second reminding information upon receipt of the second reminding control signal. For example, the first reminding information and the second reminding information may be different from each other.

According to an exemplary embodiment of the present invention, the fatigue state determination module comprises a third communication unit and a fatigue state determination unit for determining whether the brain of the testee is in a fatigue state according to the final sample entropy value and for generating a corresponding reminding control signal. The reminding information generation module comprises a fourth communication unit, a reminding signal generation unit, an audio storage unit and an audio play unit. The third communication unit is used for sending the reminding control signal to the fourth communication unit which sends the reminding control signal to the reminding signal generation unit upon receipt of the reminding control signal. The reminding signal generation unit can send a play signal to the audio storage unit upon receipt of the reminding control signal, so as to play the audio stored in the audio storage unit via the audio play unit.

According to an exemplary embodiment of the present invention, the reminding information generation module further comprises a vibration generation unit and a vibration conduction unit, and upon receipt of the reminding control signal, the fourth communication unit sends the reminding control signal to the reminding signal generation unit which can send out a vibration start signal to the vibration generation unit upon receipt of the reminding control signal, so as to generate, via the vibration generation unit, a vibration which is transmitted to the testee via the vibration conduction unit. For example, the vibration conduction unit may be fixedly connected to the vibration generation unit.

According to an exemplary embodiment of the present invention, the apparatus comprises a wear body on which the electroencephalogram signal collection module and the reminding information generation module are disposed. The electroencephalogram signal collection module comprises a main collection electrode and a reference electrode, the audio play unit comprises a bone conduction headset, and the vibration conduction unit comprises a vibration terminal. The wear body is formed as a curved rod-like component, so that the wear body can be worn on the head of the testee. The main collection electrode is disposed on one end of the wear body to be able to fit on the prefrontal cortex of the testee, the reference electrode is disposed on the other end of the wear body to be able to fit behind the testee's ear(s), and the audio play unit is disposed on the wear body and on the same end with the reference electrode. The audio play unit and the reference electrode are disposed in such a way that when the reference electrode fits behind the testee's ear(s), the audio play unit is able to fit in the testee's ear(s). The vibration conduction unit is disposed in the middle of the wear body while protruding towards the center of the wear body.

When a person is clear-headed, brain neurons are highly excited, the brain receives huge information from the outside world, neuronal activities are highly random, and electroencephalogram signals are much complex. When the degree of fatigue of the brain increases, the degree of suppression of brain neurons increases, the brain receives less information from the outside world, the orderliness of neuronal activities increases, and similar periodic activities of electroencephalogram signals are enhanced, causing the degree of complexity of electroencephalogram signals decline. Therefore, the sample entropy algorithm can be used to calculate the sample entropy value of electroencephalogram signals, and the degree of fatigue of a testee's brain can be objectively and accurately evaluated according to the sample entropy value.

BRIEF DESCRIPTION OF THE DRAWINGS

To more clearly illustrate the technical solution of embodiments of the present invention, the accompanying drawings of the embodiments will be briefly described below. Apparently, the accompanying drawings in the following description merely relate to some embodiments of the present invention but are not meant to limit the present invention, in which.

DETAILED DESCRIPTION

To make the purpose, technical solution and advantages of the embodiments of the present invention more clear, the technical solution of the embodiments of the present invention will be clearly and comprehensively described below with reference to the accompanying drawings of the embodiments of the present invention. Obviously, the described embodiments are merely part of, instead of all of, embodiments of the present invention. Based on the embodiments of the present invention described, all the other embodiments obtained by those of ordinary skill in the art without creative efforts fall within the scope of protection of the present invention.

Figure 1:
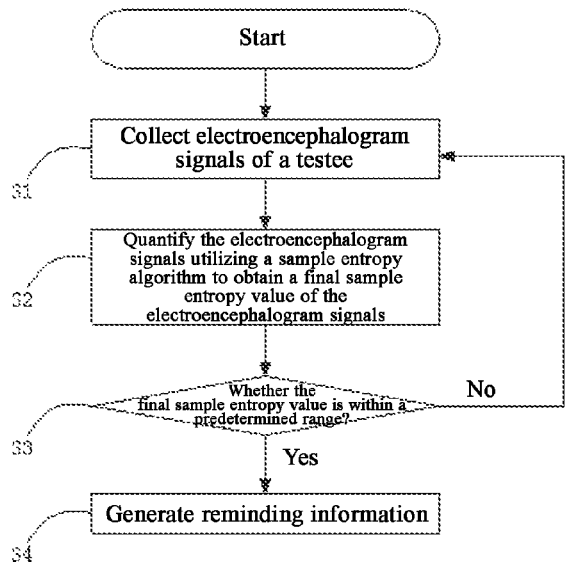
FIG. 1 is a flow chart of a method for determining whether the brain is fatigued, which is provided according to an embodiment of the present invention.
Figure 2:
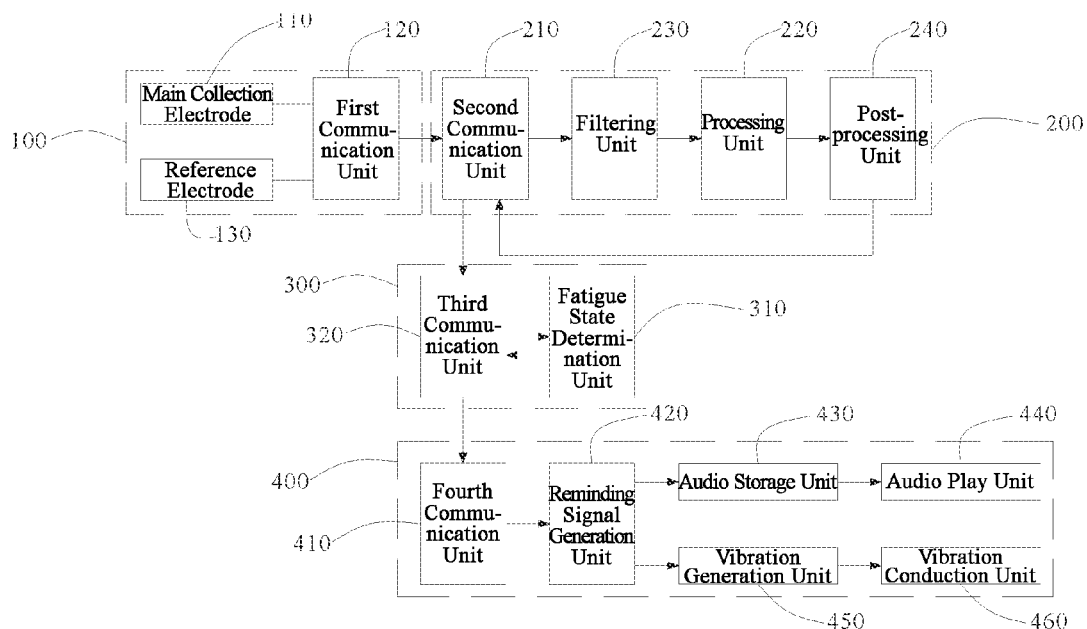
FIG. 2 is a schematic module diagram of an apparatus for determining whether the brain is fatigued, which is provided according to an embodiment of the present invention.
Figure 3:
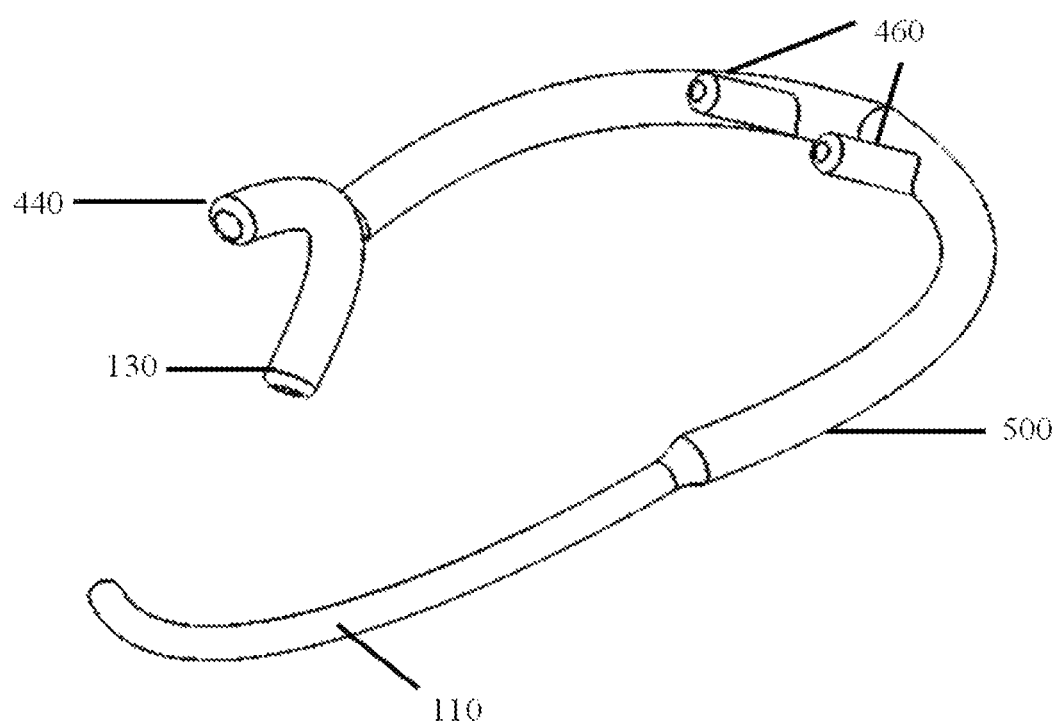
FIG. 3 is a schematic diagram of part of an apparatus for determining whether the brain is fatigued, which is provided according to an embodiment of the present invention.

As shown in FIG. 1, according to an embodiment of the present invention, there is provided a method for determining whether the brain is fatigued, wherein the method comprises:

S1. collecting electroencephalogram signals of a testee;

S2. quantifying the electroencephalogram signals utilizing a sample entropy algorithm to obtain a final sample entropy value of the electroencephalogram signals;

S3. determining whether the brain of the testee is fatigued according to the final sample entropy value, wherein it is determined that the brain of the testee is in a fatigue state when the final sample entropy value is within a predetermined range.

According to an exemplary embodiment of the present invention, the electroencephalogram signals of the testee may be collected in real time.

The sample entropy algorithm is an algorithm for calculating irregularity or complexity of time series. The greater the randomness of the electroencephalogram signals and the higher the complexity, the larger the sample entropy value is; on the contrary, the more regular the electroencephalogram signals are, the smaller the sample entropy value is.

When a person is clear-headed, brain neurons are highly excited, the brain receives huge information from the outside world, neuronal activities are highly random, and electroencephalogram signals are much complex. When the degree of fatigue of the brain increases, the degree of suppression of brain neurons increases, the brain receives less information from the outside world, orderliness of neuronal activities increases, and similar periodic activities of electroencephalogram signals are enhanced, causing the degree of complexity of the electroencephalogram signals decline. Therefore, the sample entropy algorithm can be used to calculate the sample entropy value of electroencephalogram signals, and the degree of fatigue of the testee's brain can be objectively and accurately evaluated according to the sample entropy value.

As described hereinabove, the higher the sample entropy value is, the more clear the testee's brain is, while the lower the sample entropy value is, then the higher the degree of fatigue of the testee's brain is. Typically, a sample entropy value is a decimal between 0 and 1. The testee can set end values of the predetermined range by himself.

According to an exemplary embodiment of the present invention, the predetermined range is [0,0.8]. When the sample entropy value is within the range [0,0.8], it is determined that the brain of the testee is in a fatigue state. In the step S3, when the final sample entropy value is within the range (0.8,1], it is determined that the brain of the testee is in an active state and it proceeds to the step S1.

Different degrees of fatigue affect behaviors of the testee differently, and the corresponding ways to relieve fatigue are different. Thus, the degrees of fatigue can be classified into mild and excessive fatigue. Accordingly, the predetermined range comprises a first predetermined sub-range [0, 0.5] and a second predetermined sub-range (0.5, 0.8]. When the final sample entropy value is within the first predetermined sub-range, it is determined that the brain of the testee is in an excessive fatigue state, and when the final sample entropy value is within the second predetermined sub-range, it is determined that the brain of the testee is in a mild fatigue state.

After a determination result is generated in the step S3, a display device may be utilized to display the determination result, and reminding information may also be generated according to the determination result generated in the step S3 to remind that the testee has already been in a fatigue state.

According to an exemplary embodiment of the present invention, when it is determined in the step S3 that the brain of the testee is in a fatigue state, the method further comprises:

S4. generating reminding information.

After receiving the reminding information, the testee should stop working and have a rest or conduct other relief activities.

As described hereinabove, according to the different degrees of fatigue, the brain fatigue of the testee is classified into a mild fatigue and an excessive fatigue. Accordingly, the reminding information comprises first reminding information and second reminding information, and the step S4 comprises: generating the first reminding information when the final sample entropy value is in the range [0, 0.5] (i.e., at excessive fatigue), and generating the second reminding information when the final sample entropy value is in the range (0.5, 0.8] (i.e., at mild fatigue). For example, the first reminding information and the second reminding information may be different from each other.

According to the different first and second reminding information, the degree of brain fatigue of the testee may be determined more accurately, whereby different relief measures may be taken for different degrees of brain fatigue.

According to an exemplary embodiment of the present invention, the specific type of the reminding information may not be specifically defined. For example, the reminding information may comprise audio reminding information and/or vibration reminding information.

The audio reminding information may be soothing music, and when it is determined that the brain of the testee is in a fatigue state, soothing music may be played, so that the testee's brain gets relaxed and rest.

In case that the reminding information comprises the vibration reminding information, when feeling the vibration reminding information, the testee may stop working and have a rest. Optionally, in the step S4, the vibration reminding information may be applied to the testee's Fengchi acupoint. Applying the vibration reminding information to the Fengchi acupoint is equivalent to massage on the Fengchi acupoint, which can relieve fatigue of the testee.

In order to make the determination result in the step S3 more accurate, according to an exemplary embodiment of the present invention, the step S2 may comprise:

S21. filtering the electroencephalogram signals to remove noise interference;

S22. quantifying the electroencephalogram signals without noises by utilizing a sample entropy algorithm, to obtain an initial sample entropy value;

S23. performing normalization processing on the initial sample entropy value to obtain the final sample entropy value.

According to another aspect of the embodiments of the present invention, there is provided an apparatus for determining whether the brain is fatigued, which apparatus may be used to execute the method for determining whether the brain is fatigued. Specifically, the apparatus comprises:

an electroencephalogram signal collection module 100 for collecting electroencephalogram signals of the testee;

a quantization processing module 200 for quantifying the electroencephalogram signals utilizing a sample entropy algorithm to obtain a final sample entropy value of the electroencephalogram signals;

a fatigue state determination module 300 for determining whether the brain of the testee is fatigued according to the final sample entropy value, wherein it is determined that the brain of the testee is in a fatigue state when the final sample entropy value is within a predetermined range.

According to an exemplary embodiment of the present invention, an input terminal of the quantization processing module 200 may be connected with an output terminal of the electroencephalogram signal collection module 100.

According to an exemplary embodiment of the present invention, an input terminal of the fatigue state determination module 300 is connected with an output terminal of the quantization processing module 200.

The electroencephalogram signal collection module 100 is used to execute the step S1, the quantization processing module 200 is used to execute the step S2, and the fatigue state determination module 300 is used to execute the step S3. As described hereinabove, the quantization processing module 200 may be utilized to quantify the degree of fatigue of the brain, so that it may be more objectively and accurately determined whether the brain of the testee is in a fatigue state or not.

According to an exemplary embodiment of the present invention, the quantization processing module 200 and the fatigue state determination module 300 may be integrated on the same circuit board, the electroencephalogram signal collection module 100 may be independent of the quantization processing module 200 and the fatigue state determination module 300, and the electroencephalogram signal collection module 100 may be connected to and communicate with the quantization processing module 200 through a wire, data line, etc., and also may communicate with the quantization processing module 200 through wireless signals. According to an exemplary embodiment of the present invention, a storage module may be disposed in the fatigue state determination module 300, and a chip implementing the sample entropy algorithm may be disposed in the quantization processing module 200.

As described hereinabove, the predetermined range may be [0,0.8]. When the final sample entropy value obtained in the quantization processing module 200 is within [0,0.8], the fatigue state determination module determines that the testee is in a brain fatigue state. Accordingly, when the final sample entropy value is within the range (0.8,1], the fatigue state determination module determines that the brain of the testee is in an active state. According to an exemplary embodiment of the present invention, the range (0.8,1] may be stored in the fatigue state determination module 300.

According to an exemplary embodiment of the present invention, the specific structure of the electroencephalogram signal collection module is not specially defined as long as it can collect electroencephalogram signals. According to an exemplary embodiment of the present invention, the electroencephalogram signal collection module 100 may comprise a main collection electrode 110 for being disposed at a position of the prefrontal cortex of the testee, and a first communication unit 120 for outputting the electroencephalogram signals to the quantization processing module 200. The main collection electrode 110 is used for collecting electroencephalogram signals of the testee, and is electrically connected to the first communication unit 120. The quantization processing module 200 comprises a second communication unit 210 for communicating with the first communication unit 120 and a processing unit 220 for performing quantization of the electroencephalogram signals. The first communication unit 120 is formed as the output terminal of the electroencephalogram signal collection module 100, and the second communication unit 210 is formed as the input terminal of the quantization processing module 200.

According to an exemplary embodiment of the present invention, the processing unit 220 may directly conduct the sample entropy algorithm on the electroencephalogram signals and take the directly calculated sample entropy value as the final sample entropy value.

To make the sample entropy value obtained by the quantization processing module 200 more comply with the real electroencephalogram state, according to an exemplary embodiment of the present invention, the quantization processing module 200 further comprises a filtering unit 230 and a post-processing unit 240. The filtering unit 230 is used for filtering the received electroencephalogram signals to remove noise interference, the processing unit 220 is used for quantifying the electroencephalogram signals without noises by utilizing the sample entropy algorithm, so as to obtain an initial sample entropy value, and the post-processing unit 240 is used for performing normalization processing on the initial sample entropy value to obtain the final sample entropy value.

According to an exemplary embodiment of the present invention, the main collection electrode 110 may be a dry-state electrode, and utilizing the dry-state electrode to collect electroencephalogram signals may reduce the difficulty of collecting electroencephalogram signals.

The first communication unit 120 and the second communication unit 210 may communicate with each other through a data line. To simplify the structure and not to affect the activity of the testee during the collection of electroencephalogram signals, according to an exemplary embodiment of the present invention, both the first communication unit 120 and the second communication unit 210 are wireless communication units. After wearing the electroencephalogram signal collection module 100, the testee may move freely without affecting his/her normal work and life.

To collect more accurate and real electroencephalogram signals, according to an exemplary embodiment of the present invention, the electroencephalogram signal collection module 100 may further comprise a reference electrode 130 for being disposed behind the ear(s) of the testee and for collecting electroencephalogram signals of the testee, where the reference electrode is also electrically connected with the first communication unit 120.

As described hereinabove, the predetermined range comprises a first predetermined sub-range [0, 0.5] and a second predetermined sub-range (0.5, 0.8]. When the final sample entropy value is within the first predetermined sub-range, it is determined that the brain of the testee is in an excessive fatigue state, and when the final sample entropy value is within the second predetermined sub-range, it is determined that the brain of the testee is in a mild fatigue state.

To remind the testee, according to an exemplary embodiment of the present invention, the apparatus may further comprise a reminding information generation module 400. The fatigue state determination module 300 can generate a reminding control signal when determining that the brain of the testee is in a fatigue state and send the reminding control signal to the reminding information generation module 400 which can generate reminding information according to the reminding control signal.

To facilitate the testee in knowing his/her current brain fatigue state, according to an exemplary embodiment of the present invention, the reminding control signal comprises a first reminding control signal and a second reminding control signal. The fatigue state determination module 300 can generate the first reminding control signal when the final sample entropy value is within the range [0, 0.5] and generate the second reminding control signal when the final sample entropy value is within the range (0.5, 0.8]. The reminding information comprises first reminding information and second reminding information. The reminding information generation module 400 can generate the first reminding information upon receipt of the first reminding control signal and generate the second reminding information upon receipt of the second reminding control signal. For example, the first reminding information and the second reminding information may be different from each other.

According to an exemplary embodiment of the present invention, the fatigue state determination module 300 may comprise a third communication unit 320, and a fatigue state determination unit 310 for determining whether the brain of the testee is in a fatigue state according to the final sample entropy value and for generating a corresponding reminding control signal. The reminding information generation module 400 comprises a fourth communication unit 410, a reminding signal generation unit 420, an audio storage unit 430 and an audio play unit 440. The third communication unit 320 is used for sending the reminding control signal to the fourth communication unit 410 which transmits the reminding control signal to the reminding signal generation unit 420 upon receipt of the reminding control signal. The reminding signal generation unit 420 can send a play signal to the audio storage unit 430 upon receipt of the reminding control signal, so as to play audio stored in the audio storage unit 430 via the audio play unit 440.

The audio stored in the audio storage unit 430 may be soothing music, and the audio play unit 440 may be a stereo and may also be a headset. The third communication unit 320 and the fourth communication unit 420 may be connected with each other via a data line, and may also communicate with each through wireless signals.

According to an exemplary embodiment of the present invention, the reminding information generation module 400 further comprises a vibration generation unit 450 and a vibration conduction unit 460. Upon receipt of the reminding control signal, the fourth communication unit 410 transmits the reminding control signal to the reminding signal generation unit 420 which can send out a vibration start signal to the vibration generation unit 450 upon receipt of the reminding control signal, so as to generate a vibration via the vibration generation unit 450, where the vibration is transmitted to the testee via the vibration conduction unit 460. The vibration generation unit 450 may be fixedly connected to the vibration conduction unit 460, so that the vibration signal is delivered from the vibration generation unit to the vibration signal conduction unit.

According to an exemplary embodiment of the present invention, the apparatus may comprise a wear body 500, on which the electroencephalogram signal collection module 100 and the reminding information generation module 400 are disposed. The electroencephalogram signal collection module 100 comprises a main collection electrode 110 and a reference electrode 130, the audio play unit 440 comprises a bone conduction headset, and the vibration conduction unit 460 comprises a vibration terminal. The wear body 500 may be formed as a curved rod-like component, so that the wear body 500 can be worn on the head of the testee. The main collection electrode 110 is disposed on one end of the wear body 500 to be able to fit on the prefrontal cortex of the testee, the reference electrode 130 is disposed on the other end of the wear body 500 to be able to fit behind the testee's ear(s), and the audio play unit 440 is disposed on the wear body 500 and on the same end with the reference electrode 130. The audio play unit 440 and the reference electrode 130 are disposed in such a way that when the reference electrode 130 fits behind the testee's ear(s), and the audio play unit 440 is able to fit in the testee's ear(s). The vibration conduction unit 460 is disposed in the middle of the wear body 500 while protruding towards the center of the wear body 500.

When the determination of the brain fatigue state of the testee is performed, the wear body 500 is worn on the brain of the testee, the reference electrode 130 fits behind an ear of the testee, the audio play unit 440 fits in the ear close to the reference electrode 130, the main collection electrode 110 fits on the prefrontal cortex of the testee, and the vibration conduction unit 460 is pressed on the Fengchi acupoint of the testee.

When the fatigue state determination module determines that the testee is in a brain fatigue state, the audio play unit starts to play soothing music, the vibration conduction unit 460 receives the vibration from the vibration generation unit 450 and the testee's Fengchi acupoint is massaged to achieve the purpose of relieving fatigue.

It will be understood that the above description is merely about exemplary embodiments of the present invention and is not meant to limit the scope of the present invention, and the scope of the present invention is defined by the appended claims. Those of ordinary skill in the art may make various variations and improvements, without departing from the spirit and essence of the present invention, and these variations and improvements also fall within the scope of the present invention.

What is claimed is:

1. An apparatus for determining whether the brain is fatigued, the apparatus comprising:
    an electroencephalogram signal collector configured to collect electroencephalogram signals of a testee;
    a quantization processor configured to quantify the electroencephalogram signals according to randomness of the electroencephalogram signals to obtain a final sample entropy value of the electroencephalogram signals, wherein electroencephalogram signals with greater randomness are quantified to have a larger final sample entropy value;
    a fatigue state identifier configured to determine whether the brain of the testee is fatigued according to the final sample entropy value, wherein the fatigue state identifier is configured to generate a reminder control signal in response to a determination that the brain of the testee is in a fatigue state when the final sample entropy value is within a first predetermined range, the first predetermined range comprising a first predetermined sub-range [0, 0.5] and a second predetermined sub-range (0.5, 0.8]; and
    a reminder information generator configured to generate reminder information according to the reminder control signal from the fatigue state identifier, wherein the reminder information includes at least one of audio reminder information and vibration reminder information;
    wherein the reminder control signal includes a first reminder control signal and a second reminder control signal, and the fatigue state identifier is configured to generate the first reminder control signal when the final sample entropy value is within the first predetermined sub-range and to generate the second reminder control signal when the final sample entropy value is within the second predetermined sub-range, and wherein the reminder information comprises first reminder information and second reminder information, and the reminder information generator is configured to generate the first reminder information upon receipt of the first reminder control signal and generate the second reminder information upon receipt of the second reminder control signal.

2. The apparatus according to claim 1, wherein the first predetermined range is [0,0.8], and when the final sample entropy value is within a second predetermined range (0.8, 1], the fatigue state identifier is configured to determine that the brain of the testee is in an active state.

3. The apparatus according to claim 1, wherein the electroencephalogram signal collector comprises:
    a main collection electrode configured to be disposed at a position of the prefrontal cortex of the testee and collect the electroencephalogram signals of the testee; and
    a first communication circuit configured to output the electroencephalogram signals from the main collection electrode to the quantization processor, the main collection electrode electrically connected to the first communication circuit which comprises an output terminal of the electroencephalogram signal collector, wherein the quantization processor comprises:
    a second communication circuit configured to receive the electroencephalogram signals from the first communication circuit, the second communication circuit comprising an input terminal of the quantization processor; and
    a processing circuit configured to perform quantization of the electroencephalogram signals.

4. The apparatus according to claim 3, wherein both the first communication circuit and the second communication circuit are wireless communication circuits.

5. The apparatus according to claim 3, wherein the electroencephalogram signal collector further comprises a reference electrode configured to be disposed behind the ear(s) of the testee and collect the electroencephalogram signals of the testee, the reference electrode also electrically connected with the first communication circuit.

6. The apparatus according to claim 3, wherein the quantization processor further comprises a filtering circuit configured to filter the received electroencephalogram signals received from the second communication circuit to remove noise interference, the processing circuit configured to quantify the electroencephalogram signals without noises according to randomness of the electroencephalogram signals without noises to obtain an initial sample entropy value; and a post-processing circuit configured to perform normalization processing on the initial sample entropy value provided by the processing circuit to obtain the final sample entropy value.

7. The apparatus according to claim 1, wherein the fatigue state identifier comprises:
    a fatigue state determination circuit configured to determine whether the brain of the testee is in a fatigue state according to the final sample entropy value received from a third communication circuit, and generate a corresponding reminder control signal, the third communication circuit configured to send the reminder control signal to a fourth communication circuit, wherein the reminder information generator comprises:
    the fourth communication circuit configured to receive the reminder control signal from the third communication circuit, and send the reminder control signal to a reminder signal generation circuit;
    the reminder signal generation circuit configured to send a play signal to an audio storage circuit upon receipt of the reminder control signal from the fourth communication circuit;
    the audio storage circuit configured to store audio and receive the play signal from the reminder signal generation circuit; and
    an audio play circuit configured to play audio stored in the audio storage circuit.

8. The apparatus according to claim 7, wherein the reminder information generator further comprises:
    a vibration generation circuit configured to generate a vibration upon receipt of a vibration start signal from the reminder signal generation circuit, and transmit the vibration to a vibration conduction circuit, wherein the reminder signal generation circuit is configured to generate the vibration start signal in response to receiving the reminder control signal from the fourth communication circuit; and the vibration conduction circuit configured to receive the vibration from the vibration generation circuit and transmit the vibration to the testee.

9. The apparatus according to claim 8, wherein the apparatus comprises a wearable device, on which the electroencephalogram signal collector and the reminder information generator are disposed, and wherein the electroencephalogram signal collector comprises a main collection electrode and a reference electrode, the audio play circuit comprises a bone conduction headset, the vibration conduction circuit comprises a vibration terminal, and the wearable device is formed as a curved rod-shaped component so that the wearable device can be worn on the head of the testee, the main collection electrode disposed on one end of the wearable device to be configured to fit on the prefrontal cortex of the testee, the reference electrode disposed on the other end of the wearable device to be configured to fit behind the testee's ear(s), the audio play circuit disposed on the wearable device and on the same end with the reference electrode, the audio play circuit and the reference electrode disposed such that the audio play circuit is configured to fit in the testee's ear(s) when the reference electrode is configured to fit behind the testee's ear(s), and the vibration conduction circuit is disposed in the middle of the wearable device while protruding towards the center of the wearable device.

* * * * *